US00PP23905P2

(12) United States Plant Patent
Ruter

(10) Patent No.: US PP23,905 P2
(45) Date of Patent: Sep. 17, 2013

(54) HOLLY PLANT NAMED 'RUTHOL1'

(50) Latin Name: *Ilex crenata×I. maximowicziana*
Varietal Denomination: RutHol1

(75) Inventor: John M. Ruter, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 58 days.

(21) Appl. No.: 13/199,218

(22) Filed: Aug. 22, 2011

(51) Int. Cl.
*A01H 5/00* (2006.01)

(52) U.S. Cl.
USPC ..... Plt./247

(58) Field of Classification Search
USPC ..... Plt./247
See application file for complete search history.

*Primary Examiner* — Kent L Bell
(74) *Attorney, Agent, or Firm* — Klarquist Sparkman, LLP

(57) ABSTRACT

A Japanese holly plant having a unique upright growth habit that makes it suitable for topiary usage, hedge plant usage and as a landscape shrub. The new plant is widest at the middle or central area, with a rounded base and pyramidal apex. The new plant has large leaves and a relatively fast growth rate for a Japanese holly plant.

3 Drawing Sheets

Latin name: *Ilex crenata×I. maximowicziana.*
Variety denomination: 'RUTHOL1'.

ORIGIN OF THE INVENTION

The present invention relates to a new and distinct variety of a Japanese holly plant named 'RutHol1'. Open pollinated seed was collected from the seed (female) parent, *Ilex crenata* 'Sky Pencil' (unpatented) plant. Growing within 20 meters of the 'Sky Pencil' plant were male hollies *I. crenata* 'Glass' (unpatented) and an unnamed plant of *I. maximowicziana* (unpatented), both of which have an overlapping period of anthesis with 'Sky Pencil'. The collected seed was planted in a cultivated area and grown. 'RutHol1' was subsequently selected while growing in this cultivated area and appears to be intermediate to *I. crenata* and *I. maximowicziana*, confirming that an unnamed plant of *I. maximowicziana* is the pollen (male) parent. The original 'RutHol1' plant is growing in Tifton, Ga.

BACKGROUND OF THE INVENTION

The primary objective of this research program was to produce a new Japanese holly variety having an upright form that is suitable for use as a hedge plant.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. A unique upright growth habit that makes it suitable for topiary usage, hedge plant usage and as a landscape shrub.
2. A plant that is widest at the middle or central area.
3. A plant with a relatively fast growth rate for a Japanese holly plant.

Asexual reproduction of this new variety by rooting stem cuttings, as performed at Tifton, Ga., shows that the foregoing and all other characteristics and distinctions come true to form and are established and transmitted through succeeding propagations.

COMPARISON WITH OTHER VARIETIES

The new 'RutHol1' plant has a much smaller height to width ratio than its parent plant 'Sky Pencil'. For example, a six year old 'RutHol1' plant had a height to width ratio of 1.5 in comparison to a height to width ratio of 3.9 for a 'Sky Pencil' plant of the same age. In addition, the height to width ratio of *Ilex maximowicziana* '10-8S' (unpatented), is much less than 'RutHol1'. An eight year old plant of this variety had a height to width ratio of 0.6 in comparison. Also, the leaves of the 'RutHol1' plant are much larger than the leaves of both 'Sky Pencil' and *Ilex maximowicziana* '10-8S'. The leaves of the new plant are typically from 3.5 cm to 4.0 cm long in comparison to leaves of these two other plants which are typically 2 cm to 3 cm long. In addition, the leaves of 'RutHol1' are generally oval in shape in comparison to the eliptic shaped leaves of 'Sky Pencil' and oblanceolate shaped leaves of *Ilex maximowicziana* '10-8S'.

Another holly utilized in the trade is *Ilex crenata* 'Steeds' (unpatented), which has an upright form that is widest at its base. This compares to 'RutHol1' which is widest in the middle. In comparison to 'Sky Pencil', 'RutHol1' is also a faster growing variety than 'Sky Pencil'. One six year old plant of the 'RutHol1' variety reached a height of 240 cm, a typical height for this age plant, in comparison to a height of 117 cm for a 'Sky Pencil' plant of the same age. In contrast, an eight year old *Ilex maximwicziana* '10-8S' had a height of 352 cm. The more rapid growth rate of 'RutHol1' in comparison with 'Sky Pencil' means that saleable number 5 containers of 'Sky Pencil' might take three or four years to grow in comparison to eighteen months to grow a saleable number 5 container containing a 'RutHol1' plant.

BRIEF DESCRIPTION OF THE ILLUSTRATIONS

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

Figure 1:
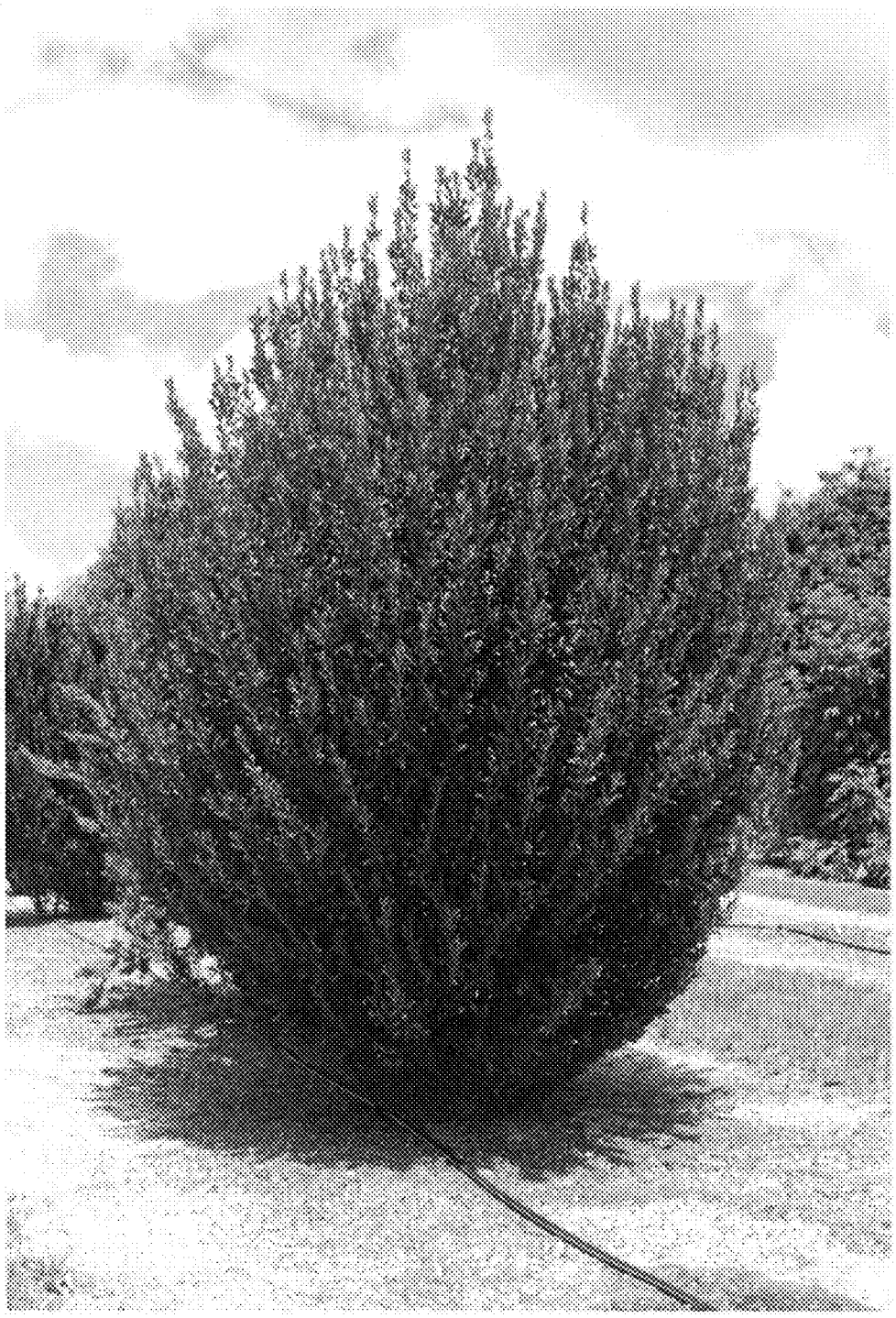
FIG. 1 is a picture of a six year old 'RutHol1' plant growing in Tifton, Ga.
Figure 2:
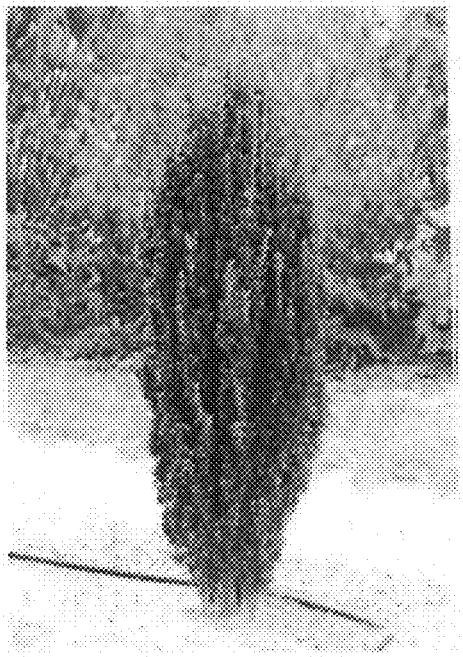
FIG. 2 is a picture of a six year old 'Sky Pencil' plant growing in Tifton, Ga. for comparison.
Figure 3:
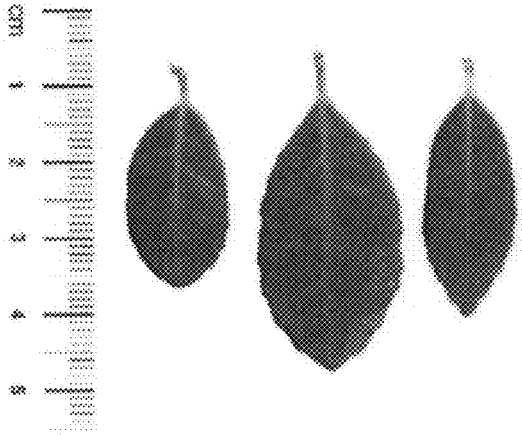
FIG. 3 is a photograph of a leaf of 'RutHol1' (center leaf) in comparison with a 'Sky Pencil' leaf to the left and an *Ilex maximowicziana* '10-8S' leaf on the right.

Certain characteristics of this variety, such as growth and color, may change with changing environmental conditions (e.g., light, temperature, moisture, nutrient availability, or other factors).

The following is a detailed description of my new holly cultivar with color descriptions using terminology in accordance with The Royal Horticultural Society (London) Colour Chart (2001), except where ordinary dictionary significance of color is indicated. The colors of an illustration of this type may vary with lighting and other conditions. Therefore, color characteristics of this new variety should be determined with reference to the observations described herein, rather than from these illustrations alone.

Parentage:

*Seed parent.*—*Ilex crenata* 'Sky Pencil'.

*Pollen parent.*—An unnamed plant of *I. maximowiczi-ana.*

Bloom:

*Size.*—Average open diameter is about 3-5 mm.

*Borne.*—On current year's growth.

*Time.*—Commonly mid to late May to early June.

*Petalage.*—Number of petals under normal conditions: four; petal length: about 0.2 cm; petal width: about 0.2 cm; apex: obtuse; margin: smooth; base: rounded.

*Color.*—Both upper and lower petal surfaces are dull Green-White at first opening (RHS 155C).

*Petal shape.*—Ovate.

*Fragrance.*—No noticeable fragrance.

*Depth.*—Approximately 5 mm.

*Sepal.*—Number: 4; shape: ovate; length and width: about 1 mm each; apex: rounded; margin: entire; color: both surfaces Yellow-Green (RHS 144 A).

*Bud.*—Shape: obtuse; length: about 2.0 mm to 2.5 mm; width (diameter): about 1.5 mm; color: Greyed-Green (RHS 197 C).

*Pedicel.*—Length: about 2 mm; diameter: about 0.5 mm; color: Yellow (RHS 144 B).

Reproductive parts:

*Sex.*—Male plant, no fruit. Flowers only male functional.

*Stamens.*—Four. Anthers: Length: 2 mm. Color: Yellow (RHS 11B). Filaments: Length: 3 mm. Color: Yellow-Green (RHS 144B). Pollen: Color: Yellow (RHS 11C).

Plant:

*Form.*—Upright hardy evergreen plant with rounded base and broadly pyramidal apex. A perennial woody shrub. Height to width ratio of six year old 'RutHol1' plant of about 1.5. Wider in middle than at base or apex.

*Growth.*—Rate: Vigorous for a Japanese holly plant. Typical internode length 1.0-1.5 cm, same as 'Sky Pencil'. Height: 240 cm after six years in Tifton, Ga. Width: 163 cm after six years in Tifton, Ga.

*Rootstock.*—Own root stock.

*Bark.*—Smooth: Greyed-Orange (RHS 175 C).

Foliage (leaves):

*General.*—Evergreen, broad and simple.

*Leaf size.*—About 3.5 cm to 4.0 cm long; about 1.3 cm wide.

*Color.*—Adaxial leaf color: Green (RHS 137 B). Abaxial leaf color: Yellow-Green (RHS 146 C).

*Shape.*—Oval.

*Base.*—Acute.

*Apex.*—Acute.

*Texture.*—Glabrous.

*Arrangement.*—Alternate.

*Margins.*—Typically 9-13 serrations per side.

*Petiole.*—Color: Yellow-Green (144 A); length: 2 to 3 mm; width (diameter): 0.5 to 1.0 mm.

*Vein color.*—Yellow-Green (RHS 146C).

*Venation pattern.*—Pinnate.

Disease and pest resistance: Appears to be resistant to spider mites.

Wood:

*Stems.*—Wood: Current season's growth — color Yellow(RHS 144A). Stems of 1-2 years age — color Yellow-Green (RHS 152A). Older stems, older than 2 years — color Yellow-Green (RHS 152A). Typical stem diameters: 1 year stem: 2-3 mm; 2 year stems: 5-8 mm; 3 year stems: up to 15 mm.

Winter hardiness: The plants have been grown in USDA zone 8a. The 'RutHol1' plants have survived temperatures as low as 16° F. without any visible damage.

I claim:

1. A new and distinct variety of holly plant, substantially as herein shown and described.

* * * * *